(12) United States Patent
Farrell

(10) Patent No.: US 12,128,190 B2
(45) Date of Patent: Oct. 29, 2024

(54) MEDICAL DEVICE PRODUCTS INCLUDING LIQUID-DRAWING MEMBERS

(71) Applicant: Hollister Incorporated, Libertyville, IL (US)

(72) Inventor: David J. Farrell, Ballina (IE)

(73) Assignee: Hollister Incorporated, Libertyville, IL (US)

( * ) Notice: Subject to any disclaimer, the term of this patent is extended or adjusted under 35 U.S.C. 154(b) by 71 days.

(21) Appl. No.: 17/996,767

(22) PCT Filed: Apr. 29, 2021

(86) PCT No.: PCT/US2021/029992
§ 371 (c)(1),
(2) Date: Oct. 20, 2022

(87) PCT Pub. No.: WO2021/222642
PCT Pub. Date: Nov. 4, 2021

(65) Prior Publication Data
US 2023/0166075 A1 Jun. 1, 2023

Related U.S. Application Data

(60) Provisional application No. 63/018,730, filed on May 1, 2020.

(51) Int. Cl.
*A61M 25/00* (2006.01)
(52) U.S. Cl.
CPC ...... *A61M 25/002* (2013.01); *A61M 25/0045* (2013.01); *A61M 2025/0046* (2013.01)
(58) Field of Classification Search
CPC ............ A61M 25/002; A61M 25/0045; A61M 2025/0046

USPC .......................................................... 206/364
See application file for complete search history.

(56) References Cited

U.S. PATENT DOCUMENTS

| 5,616,119 A | 4/1997 | Davis |
| 6,065,597 A | 5/2000 | Pettersson et al. |
| 7,380,658 B2 | 6/2008 | Murray et al. |
| 9,038,822 B2 | 5/2015 | Barnell |
| 9,095,324 B2 | 8/2015 | Peck et al. |

(Continued)

FOREIGN PATENT DOCUMENTS

| EP | 1312385 A1 | 5/2003 |
| EP | 2060296 A1 | 5/2009 |

(Continued)

OTHER PUBLICATIONS

International Search Report and Written Opinion for PCT/US2021/029992 Dated Sep. 16, 2021.

*Primary Examiner* — Jacob K Ackun
(74) *Attorney, Agent, or Firm* — Cook Alex Ltd.

(57) ABSTRACT

A medical device product (10) comprises a package (12) defining an interior cavity (14), an activating liquid located within the interior cavity of the package, and a medical device (18) located within the interior cavity of the package. At least one portion of the medical device is activated by absorbing an amount of the activating liquid. A liquid-drawing member (20) is located within the interior cavity of the package. The liquid-drawing member absorbs any excess activating liquid within the cavity that was not absorbed by the at least one portion of the medical device.

14 Claims, 2 Drawing Sheets

(56) References Cited

U.S. PATENT DOCUMENTS

| | | | |
|---|---|---|---|
| 2008/0319423 A1* | 12/2008 | Tanghoj | B65D 77/20 |
| | | | 206/364 |
| 2010/0087801 A1* | 4/2010 | Torstensen | A61M 25/002 |
| | | | 206/364 |
| 2014/0360896 A1* | 12/2014 | Torstensen | A61M 25/002 |
| | | | 206/364 |
| 2015/0265801 A1 | 9/2015 | Rostami | |
| 2015/0306342 A1 | 10/2015 | Rostami et al. | |
| 2016/0346072 A1 | 12/2016 | Kawashima | |
| 2017/0015066 A1 | 1/2017 | Herrmann et al. | |
| 2017/0152066 A1 | 1/2017 | Herrmann et al. | |
| 2018/0021481 A1 | 1/2018 | Mn et al. | |
| 2019/0224384 A1 | 7/2019 | Lundahl et al. | |
| 2023/0166075 A1* | 6/2023 | Farrell | A61M 25/002 |
| | | | 206/364 |

FOREIGN PATENT DOCUMENTS

| | | |
|---|---|---|
| JP | 2000281144 A | 10/2000 |
| JP | 2001130634 A | 5/2001 |
| WO | 2014093056 A1 | 6/2014 |
| WO | 2015065725 A1 | 5/2015 |

* cited by examiner

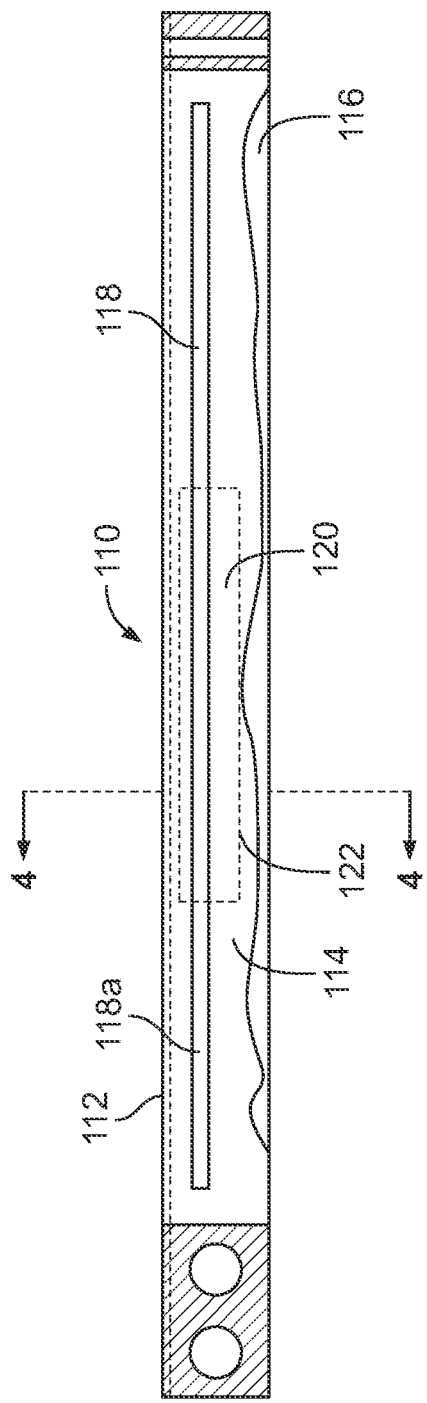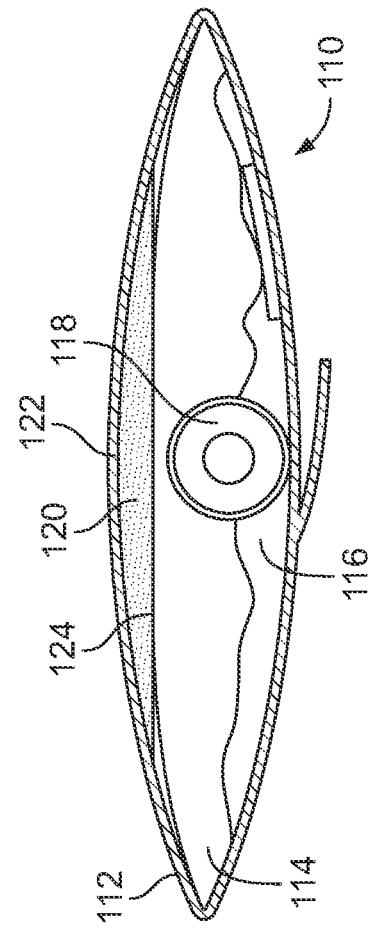

MEDICAL DEVICE PRODUCTS INCLUDING LIQUID-DRAWING MEMBERS

The present application is the U.S. National Stage Application of PCT Application No. PCT/US2021/029992, filed Apr. 29, 2021, which claims the benefit of and priority to U.S. Provisional Application No. 63/018,730, filed May 1, 2020, all of which is are hereby incorporated herein by reference.

BACKGROUND

Field of the Disclosure

The present disclosure generally relates to medical device products. More particularly, the present disclosure relates to medical device products including liquid drawing members.

Description of Related Art

Certain medical device products depend on liquid activation. One such medical device is a hydrophilic intermittent urinary catheter, in which the hydrophilic coating may be activated by direct contact of a liquid activation medium (e.g., liquid water) with the hydrophilic coating. Some of these medical device products achieve direct liquid contact by providing a package which contains the device and liquid, wherein the device is in direct contact with the liquid. In several of these products the liquid flows freely within the cavity of the package and has unobstructed access to the medical device. Because of the free flow of loose liquid within the package and unobstructed access to the device surface, it is easy to provide direct contact of the liquid medium with the device within the package.

One of the challenges of the medical device products described above is that the liquid can tend to spill from the package as the user handles the product and removes the device from the package for use. Accordingly, there is a need for products and packages that reduce the risk of liquid spillage from the package.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a medical device product includes a package defining an interior cavity, an activating liquid located within the interior cavity of the package, and a medical device located within the interior cavity of the package. At least one portion of the medical device is activated by absorbing an amount of the activating liquid. Additionally, a liquid-drawing member is located within the interior cavity of the package. The liquid-drawing member absorbs any excess activating liquid within the cavity that was not absorbed by the at least one portion of the medical device.

In another aspect, a urinary catheter product includes a package defining an interior cavity, an activating liquid located within the interior cavity of the package, and a urinary catheter located within the interior cavity of the package. At least one portion of the catheter comprises a lubricious hydrophilic material that is activated by absorbing an amount of the activating liquid. Furthermore, a liquid-drawing member is located within the interior cavity of the package. The liquid-drawing member absorbs any excess activating liquid within the cavity that was not absorbed by the at least one portion of the catheter.

BRIEF DESCRIPTION OF THE DRAWINGS

FIG. 3 is a top view of an embodiment of a package for a medical device product, according to an aspect of the present disclosure;

FIG. 4 is a cross-sectional view of the package of FIG. 3.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

Figure 1:
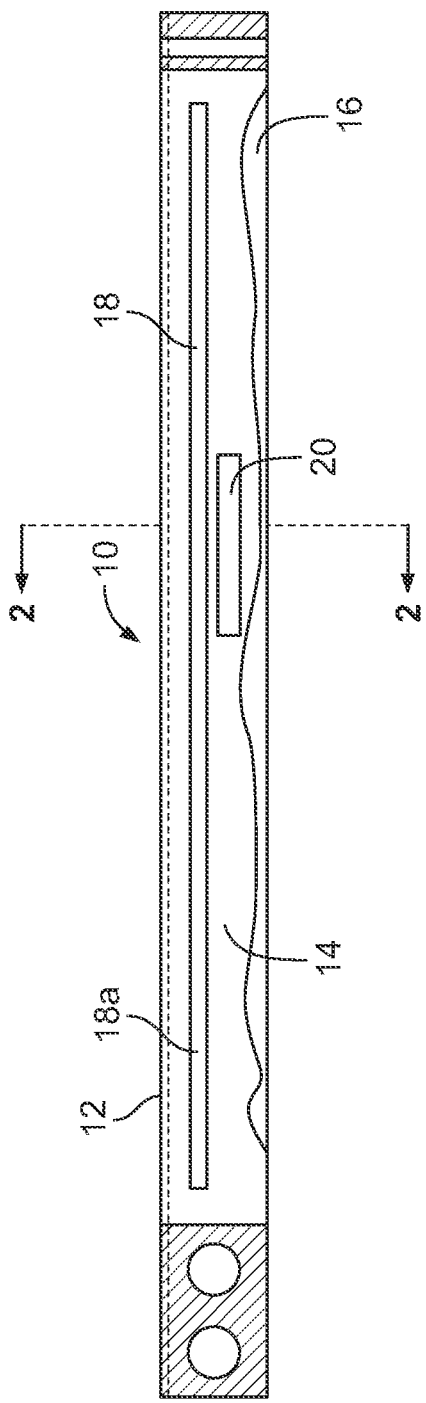
FIG. 1 is a top view of an embodiment of a package for a medical device product, according to an aspect of the present disclosure.
Figure 2:
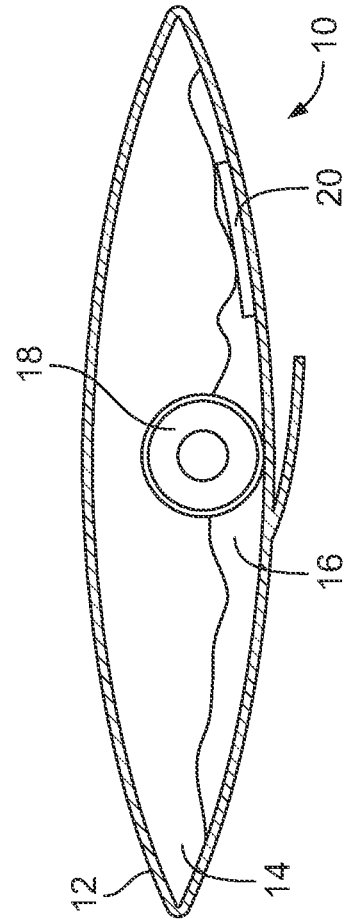
FIG. 2 is a cross-sectional view of the package of FIG. 1.

FIGS. 1 and 2 illustrate an embodiment of a medical device product 10. The medical device product may be any product that requires liquid for activation and/or assists in storing or preserving the product. The medical device product 10 comprises a package 12 defining an interior cavity 14. An activating liquid 16 and a medical device 18 are located within the interior cavity 14 of the package 12. The medical device may be any medical device that is packaged with a liquid. For example, the medical device 18 may be a hydrophilic urinary catheter. The activating liquid 16 may be any liquid that activates, preserves, or conditions the medical device 18 for use. In one embodiment, the activation liquid may be a hydration medium. The hydration medium may include water or saline.

At least one portion 18a of the medical device is activated by contact with the liquid 16. For example, the portion 18a may be activated by absorbing an amount of the activating liquid 16. When the medical device is a hydrophilic catheter, the activating liquid may hydrate/activate the hydrophilic coating of the catheter, making it more lubricious and easier to insert into a user's body.

The medical device product also includes a liquid-drawing member 20 that is located within the interior cavity 14 of the package 12. The liquid-drawing member 20 absorbs any excess activating liquid 16 within the cavity 14. Excess liquid is activating liquid 16 that was not absorbed by the at least one portion 18a of the medical device 18. The amount, or type, of the liquid-drawing member 20 within the package is tuned or enough to allow the at least one portion 18a of the medical device 18 to be activated by the activating liquid 16, while the liquid-drawing member 20 absorbs any excess liquid.

In one embodiment, the liquid-drawing member 20 may comprise a desiccant. The desiccant absorbs excess activating liquid 16 within the cavity 14 so that when the package 12 is opened, there is a reduced risk of the liquid 16 spilling out of the package 12. The liquid-drawing member 20 may include a hygroscopic agent. The hygroscopic agent may be a solid, liquid or gel. The hygroscopic agent may include at least one of a glycerol or a glycerol gel. The desiccant and the hygroscopic agent both promote drawing and absorption of excess activating liquid 16.

FIGS. 3 and 4 illustrate an embodiment of a medical device product 110. The medical device product 110 is similar to that of FIGS. 1 and 2 and includes a package 112 defining an interior cavity 114, an activating liquid 116 located within the interior cavity 114 of the package 112, and a medical device 118 located within the interior cavity 114 of the package 112. In an embodiment, the medical device 118 may be a urinary catheter such that the medical device product 110 may be a urinary catheter product. At least one portion 118a of the medical device 118 is activated, preserved or conditioned by the liquid 116. A liquid-drawing member 120 is located within the interior cavity 114 of the package 112. The liquid-drawing member 120 absorbs any excess activating liquid 116 within the cavity 114. Excess liquid is activating liquid 116 that was not absorbed by the at least one portion 118a of the medical device 118.

In the embodiment shown in FIGS. 3 and 4, the liquid-drawing member 120 is located within a compartment 122 within the interior cavity 114. The compartment 122 may be at least partially defined by a liquid permeable barrier 124 (shown in FIG. 4). In the illustrated embodiment, the compartment 122 is defined by the liquid permeable barrier 124 and the sidewall of the package 112. The barrier 124 is made of a material that allows the activating liquid 116 to pass through the barrier 124. The barrier 124 may be a liquid and gas permeable membrane. The drawing member 120 draws any excess activating liquid 116 through the barrier 124 causing the excess liquid 116 to flow from the cavity 114 into the compartment 122. By drawing the excess liquid 116 out of the cavity 114, the drawing member 120 prevents spillage, while still allowing the medical device 118 to be activated and/or hydrated by the activating liquid 116. Though the product described above includes embodiments with one cavity and/or one compartment, any appropriate number of cavities and/or compartments may be used. Additionally, in alternative embodiments, the product may be configured to contain a plurality of medical devices, a plurality of liquid draw members, and/or a plurality of activating liquids.

Other variations and combinations may also be employed without departing from the scope of the present disclosure.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

What is claimed is:

1. A medical device product, comprising:
   a package defining an interior cavity;
   an activating liquid located within the interior cavity of the package;
   a medical device located within the interior cavity of the package, at least one portion of the medical device being activated, preserved or conditioned by an amount of the activating liquid
   a liquid-drawing member located within the interior cavity of the package, the liquid-drawing member absorbing any excess activating liquid within the cavity that was not absorbed by the at least one portion of the medical device; and
   wherein the liquid-drawing member is located within a compartment within the interior cavity and the compartment is at least partially defined by a liquid permeable barrier.

2. The product of claim 1, wherein the activating liquid comprises a hydration medium.

3. The product of claim 1, wherein the activating liquid comprises water.

4. The product of claim 1, wherein the liquid-drawing member comprises a desiccant.

5. The product of claim 1, wherein the liquid-drawing member comprises a hygroscopic agent.

6. The product of claim 5, wherein the hygroscopic agent comprises at least one of a glycerol or a glycerol gel.

7. The product of claim 1, wherein the medical device comprises a urinary catheter.

8. A urinary catheter product, comprising:
   a package defining an interior cavity;
   an activating liquid located within the interior cavity of the package;
   a urinary catheter located within the interior cavity of the package, at least one portion of the catheter comprising a lubricious hydrophilic material that is activated by absorbing an amount of the activating liquid;
   a liquid-drawing member located within the interior cavity of the package, the liquid-drawing member absorbing any excess activating liquid within the cavity that was not absorbed by the at least one portion of the catheter; and
   wherein the liquid-drawing member is located within a compartment within the interior cavity and the compartment is at least partially defined by a liquid permeable barrier.

9. The product of claim 8, wherein the activating liquid comprises a hydration medium.

10. The product of claim 8, wherein the activating liquid comprises water.

11. The product of claim 8, wherein the liquid-drawing member comprises a desiccant.

12. The product of claim 8, wherein the liquid-drawing member comprises a hygroscopic agent.

13. The product of claim 12, wherein the hygroscopic agent comprises at least one of a glycerol or a glycerol gel.

14. The product of claim 8, wherein the lubricious hydrophilic material comprises a hydrophilic polymer coating.

* * * * *